United States Patent [19]

Lovett

[11] Patent Number: 5,401,648
[45] Date of Patent: Mar. 28, 1995

[54] PEPTIDES HAVING PEPTIDYL TRANSFERASE INHIBITING ACTIVITY AND METHODS OF USE THEREOF

[75] Inventor: Paul S. Lovett, Baltimore, Md.

[73] Assignee: University of Maryland College Park, College Park, Md.

[21] Appl. No.: 93,858

[22] Filed: Jul. 20, 1993

[51] Int. Cl.$^6$ .................. C12N 9/00; A61K 37/00; A61K 37/02; C07K 5/00

[52] U.S. Cl. .................................. 435/184; 530/328; 530/329; 530/330; 514/16; 514/17

[58] Field of Search ............. 530/328, 329, 330; 514/16, 17; 435/184

[56] References Cited

PUBLICATIONS

Stokes et al, Plasmid vol. 26 pp. 10–19 (1991).
Namrath et al, Mol. Gen. Genet. vol. 223 pp. 65–75 (1990).
Chen et al, J. Biol. Chem, vol. 265 pp. 3161–3167 (1990).
Brückner et al, EMBO J. vol. 4 pp. 2295–2300 (1985).
Skovgaard et al, J. Bact. vol. 169 pp. 3976–3981 (1987).

*Primary Examiner*—Robert J. Hill, Jr.
*Assistant Examiner*—Sheela J. Huff
*Attorney, Agent, or Firm*—Oblon, Spivak, McClelland, Maier & Neustadt

[57] ABSTRACT

5-mer and 8-mer polypeptides have been demonstrated to inhibit peptidyl transferase and according constitutes synthetic antibiotics. Identified, sequence-specific peptides effective include Met-Val-Lys-Thr-Asp (SEQ ID NO: 1),
    Met-Lys-Lys-Ala-Asp (SEQ ID NO: 2),
    Met-Lys-Lys-Ser-Glu (SEQ ID NO: 3) and
    Met-Ser-Thr-Ser-Lys-Asn-Ala-Asp (SEQ ID NO: 4)

The polypeptides can be used as antibiotics, alone or together with a carrier.

6 Claims, 6 Drawing Sheets

Met-Val-Lys-Thr-Asp,

Met-Lys-Lys-Ala-Asp,

Met-Lys-Lys-Ser-Glu and

Met-Ser-Thr-Ser-Lys-Asn-Ala-Asp.

FIGURE 1

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 5 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:1:

Met  Val  Lys  Thr  Asp
   1                        5

( 2 ) INFORMATION FOR SEQ ID NO:2:

( i ) SEQUENCE CHARACTERISTICS:
      ( A ) LENGTH: 5 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:2:

Met  Lys  Lys  Ala  Asp
   1                        5

(2) INFORMATION FOR SEQ ID NO:3:

(i) SEQUENCE CHARACTERISTICS:
      (A) LENGTH: 5 amino acids
      (B) TYPE: amino acid
      (D) TOPOLOGY: unknown (ii) MOLECULE TYPE: peptide (xi) SEQUENCE DESCRIPTION: SEQ ID NO:3:

Met Lys Lys Ser Glu
  1               5

(2) INFORMATION FOR SEQ ID NO:4:

(i) SEQUENCE CHARACTERISTICS:
      (A) LENGTH: 8 amino acids
      (B) TYPE: amino acid
      (D) TOPOLOGY: unknown (ii) MOLECULE TYPE: peptide (xi) SEQUENCE DESCRIPTION: SEQ ID NO:4:

Met Ser Thr Ser Lys Asn Ala Asp
  1               5

(2) INFORMATION FOR SEQ ID NO:5:

(i) SEQUENCE CHARACTERISTICS:
      (A) LENGTH: 4 amino acids
      (B) TYPE: amino acid
      (D) TOPOLOGY: unknown (ii) MOLECULE TYPE: peptide (xi) SEQUENCE DESCRIPTION: SEQ ID NO:5:

Met Val Lys Thr
  1

(2) INFORMATION FOR SEQ ID NO:6:

(i) SEQUENCE CHARACTERISTICS:
      (A) LENGTH: 5 amino acids
      (B) TYPE: amino acid
      (D) TOPOLOGY: unknown (ii) MOLECULE TYPE: peptide (xi) SEQUENCE DESCRIPTION: SEQ ID NO:6:

Asp Thr Lys Val Met
  1               5

PEPTIDES HAVING PEPTIDYL TRANSFERASE INHIBITING ACTIVITY AND METHODS OF USE THEREOF

BACKGROUND OF THE INVENTION

FIELD OF THE INVENTION

This invention pertains to peptides having inhibiting activity on peptidyl transferase and otherwise capable of inhibiting bacterial ribosomal activity. Thus, the three 5-mer and 8-mer peptides disclosed find use as synthetic antibiotics.

BACKGROUND OF THE INVENTION

It is known that certain antibiotics work through a mechanism involving interruption or inhibition of translation activity at bacterial ribosomal sites. Such translation, of course, is a prerequisite for bacterial molecular synthesis.

It is further known that a variety of natural antibiotics, either directly or indirectly, inhibit peptidyl transferase, an enzyme present within the large subunit of ribosomes, Monro, "Ribosome-Catalyzed Peptidyl Transfer: Effects of Some Inhibitors of Protein Synthesis", *Journal of Molecular Biology*, 28:161–165 (1967). The antibiotic chloramphenicol is targeted to this activity, which has been associated with 23S rRNA. Knoller et al, "Unusual Resistance of Peptidyl Transferase to Protein Extraction Procedures", *Science*, 256:1416–1419 (1992).

There is a continuing demand for compounds having antibiotic activity, which would include protein synthesis inhibition, in order to respond to continuing bacterial development of antibiotic resistance. It would be preferable if the antibiotic were susceptible of easy, direct synthesis, rather than dependent on fermentation chemistry and the isolation, separate and purification problems associated therewith. The invention described hereinbelow meets these needs.

SUMMARY OF THE INVENTION

Applicant has discovered four separate synthetic amino acid sequences, three 5-mer and one 8-mer polypeptides, which give substantial or complete inhibition of peptidyl transferase activity upon incubation with the appropriate ribosomal elements and peptidyl transferase. The amino acids used are natural and conventional, and the polypeptides can be synthesized directly. The specific methods of synthesis are similarly conventional, and do not constitute an aspect of this invention.

The peptides can be used directly, or in a carrier not deleterious to the peptide, the surface or individual to which the peptide is to be administered as synthetic antibiotics, demonstrated to have a strong inhibitory effect on peptidyl transferase. The polypeptides appear to be sequence specific, as substitutions within the sequence, and reversal of order, weakens or destroys peptidyl transferase inhibitory activity.

BRIEF DESCRIPTION OF THE DRAWINGS

FIG. 1 is an illustration of the peptide sequences (SEQ ID Nos: 1–4) of the claimed invention.

DETAILED DESCRIPTION OF THE INVENTION

Figure 2:
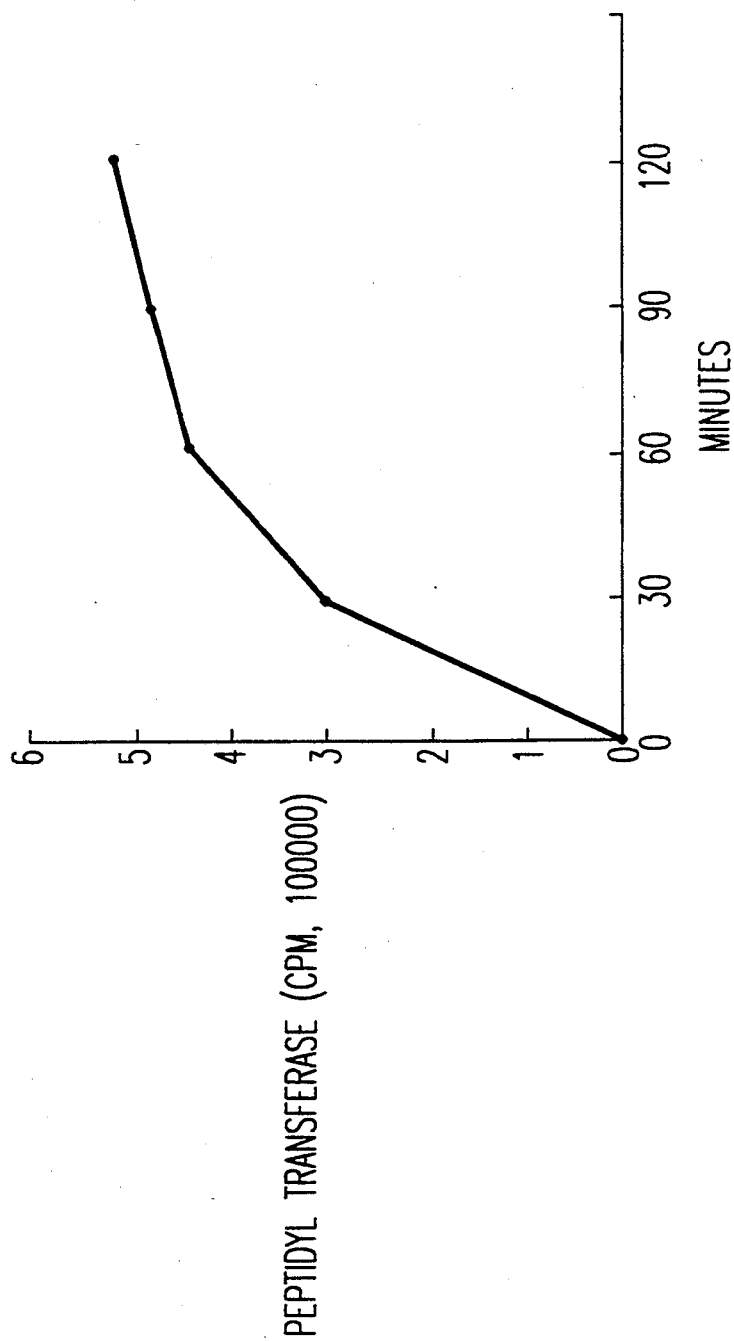
FIGS. 2 and 3 demonstrate effects of known antibiotics on peptidyl transferase by time and concentration, respectively.
Figure 3:
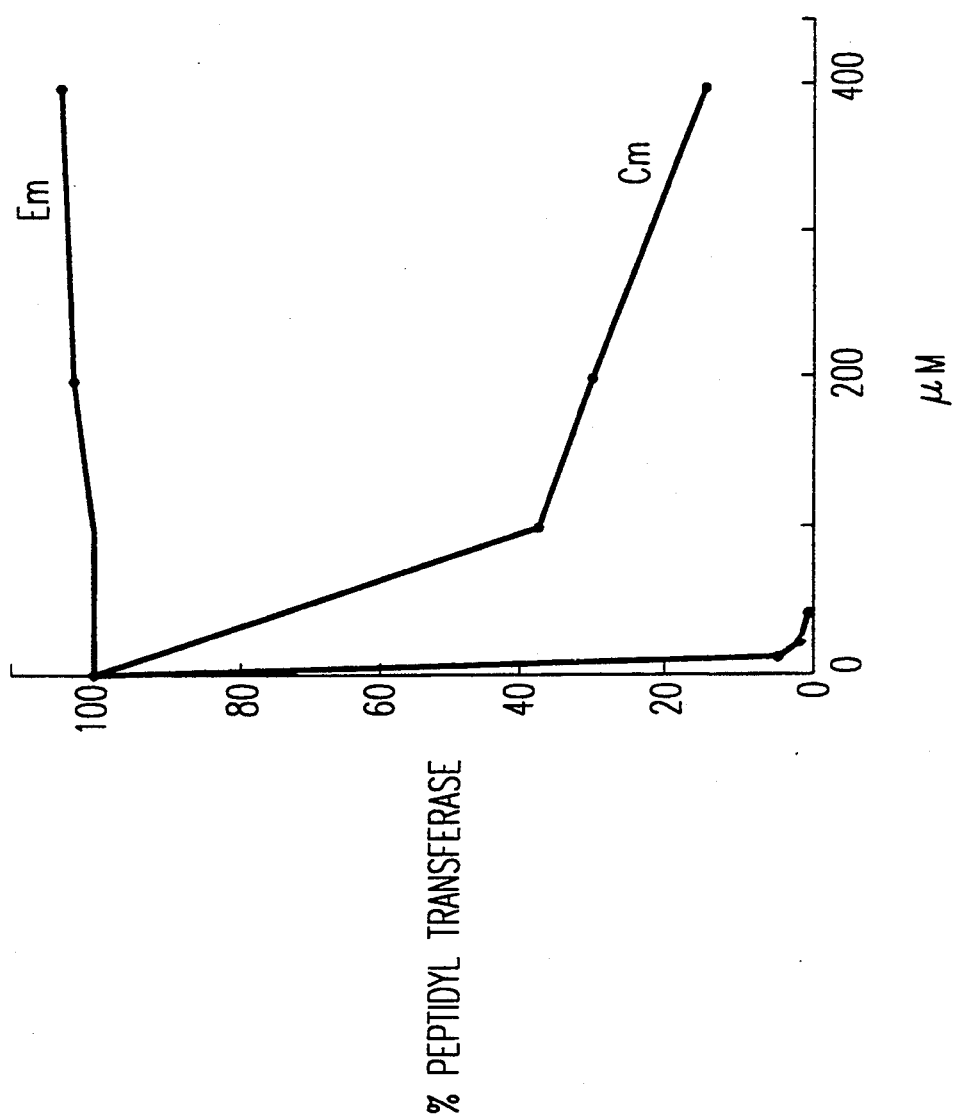
Figure 4:
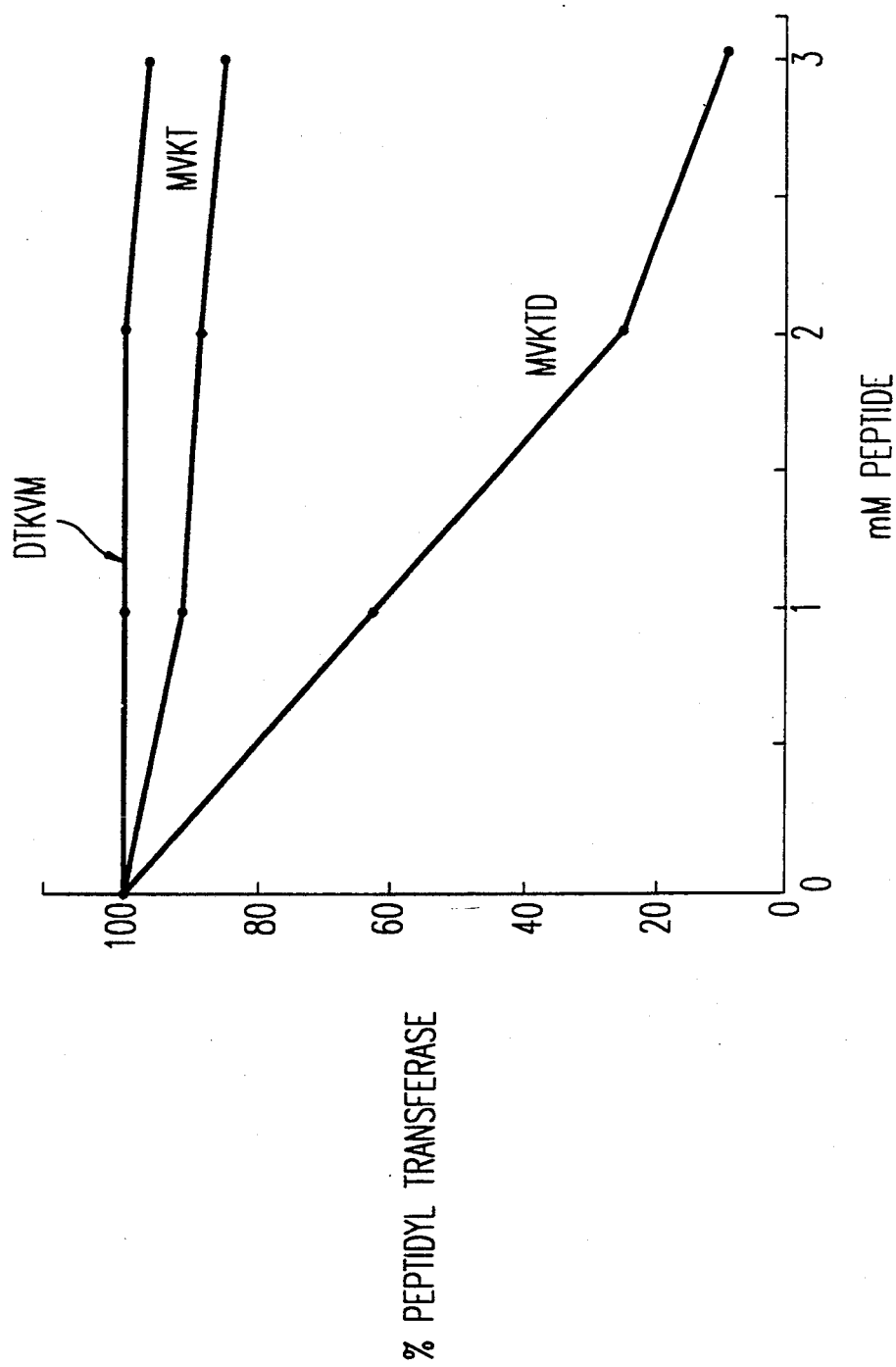
FIG. 4 graphically compares the inhibitory effect on peptidyl transferase activity by a peptide of the invention, as well as mutations thereof.
Figure 5:
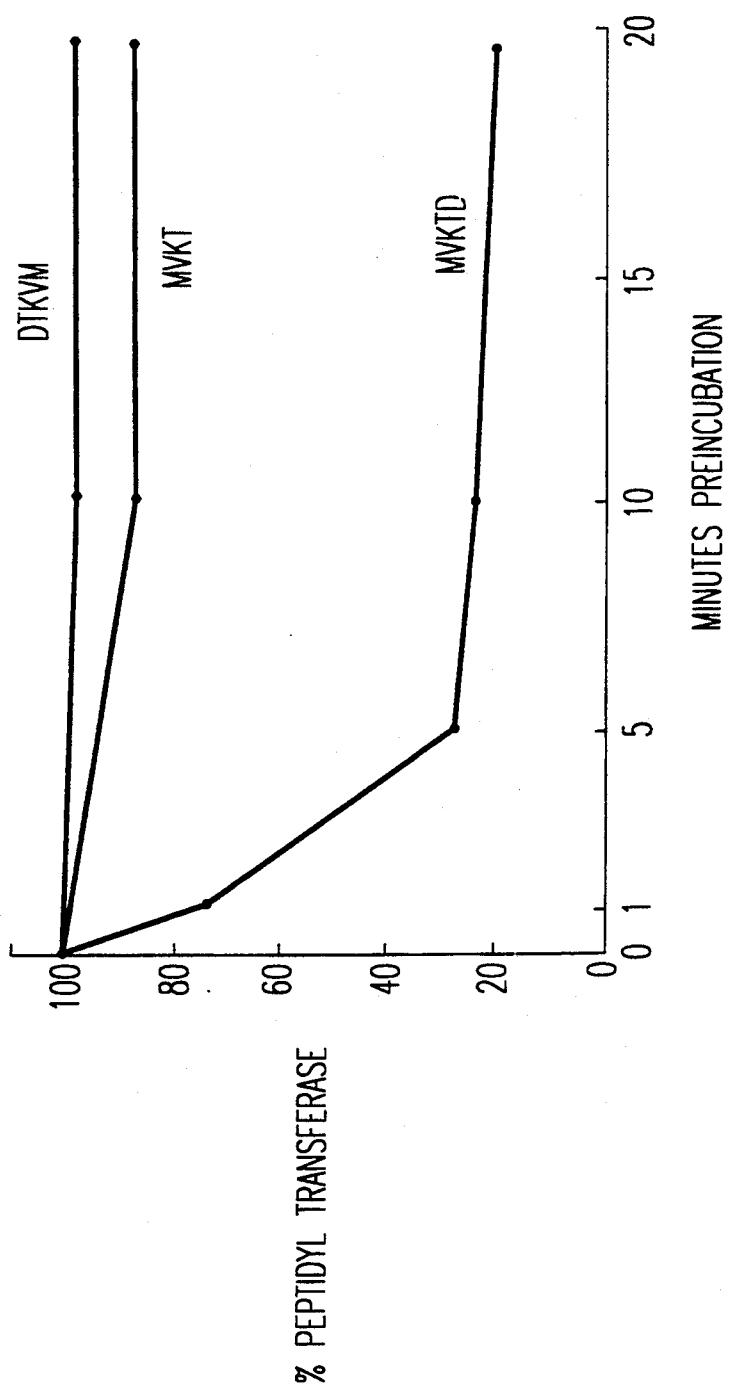
FIG. 5 demonstrates the effects of peptide-ribosome preincubation on the inhibition of peptidyl transferase for both a peptide of the claimed invention and mutations thereof.

The four peptidyl transferase inhibiting polypeptides embraced by the invention herein were obtained after intensive study of the nascent leader peptide of an inducible cat gene, a well-studied antibiotic resistance gene, see, e.g., Dubnau, "Translation Attenuation: the Regulation of Bacterial Resistance to the Macrolide-Lincosamide Streptogramin β Antibiotics", *CRIT. REV. BIOCHEM.*, 16:103–132 (1984) and Duvall et al, "Chloramphenicol Inducible Gene Expression in *Bacillus Subtilis*", Gene 24:171–177 (1983). The synthetic sequences that are the object of this invention include MVKTD (SEQ ID NO: 1)
MKKAD (SEQ ID NO: 2)
MKKSE (SEQ ID NO: 3)
MSTSKNAD (SEQ ID NO: 4)

These sequences generally correspond to leader sequences of the inducible cat gene. Thus, transcription of the gene may give rise, in vivo, to an inhibitory short-chain peptide. This method of stalling ribosomal activity, apparently through inhibition of peptidyl transferase, generally corresponds to translation attenuation, which regulates the inducible translation of other antibiotic resistance genes, such as erm. Thus, evidence strongly suggests that a general family of peptides may be used to inhibit peptidyl transferase, and ribosomal activity.

As described in detail below through comparative experiment, it has been determined that the polypeptides are sequence specific, that is, alteration of the sequence, such as reversal of the sequence, or omission of one or more of the amino acids, results in a substantial to total loss of peptidyl transferase inhibitory activity.

To be useful as effective antibiotics, the polypeptides of the claimed invention should reduce peptidyl transferase activity by at least 45 percent. All of the sequences positively identified herein exhibit such inhibitory activity. It should be noted that an effective inhibitory polypeptide may embrace more amino acids than the recited sequences, but the recited sequences, in the order recited, appear to be critical. Thus, if desired for other targeting reasons, a substantially longer chain polypeptide that did not conformally obstruct or interrupt the inhibitory activity of the 5-mer and 8-mer polypeptides of the claimed invention could exhibit peptidyl transferase inhibitory activity within the claimed invention.

Spot mutations within the polypeptides of the claimed invention, substituting known amino acids for those recited, may also be possible, where the hydrophobic/hydrophilic balance of the polypeptides, relative active sites, length and conformal characteristics are similar, may be practiced without departing from the scope of the invention.

This invention can be more clearly understood with reference to the specific examples set forth below, which illustrate the inhibitory nature of the 5-mer sequences of the invention, as well as their sequence specificity.

EXPERIMENTS

Peptidyl transferase

The fragment reaction was used to assay peptidyl transferase activity. Reaction mixes consisted of 60 mM Tris-HCl (pH 7.4), 400 mM KCl, 20 mM magnesium sulfate, and 1 mM neutralized puromycin in 50 μl, to which was added 25 μl absolute ethanol. Unless specifically noted, 70S ribosomes purified from *B. subtilis* BR151 as described in Spedding[1/] were added to 0.55 uM $^{35}$S-labeled N-formylmethionine, charged to tRNA and digested with endonuclease T1 as described by Marcker[2/], was added to each reaction at $1 \times 10^6$ to $2 \times 10^6$ cpm. Analysis of these preparations by using high-voltage paper electrophoresis demonstrated that about one-half of the radioactivity was in the N-formylmethionine-T1 fragment, with the remainder distributed between free methionine and N-formylmethionine.

[1/] *Ribosomes and Protein Synthesis*, p. 1–27 (1990).
[2/] "The formation of N-formyl-methyl-S RNA" *J. Mol. Biol.*, 14:63–70 (1965).

Figure 6:
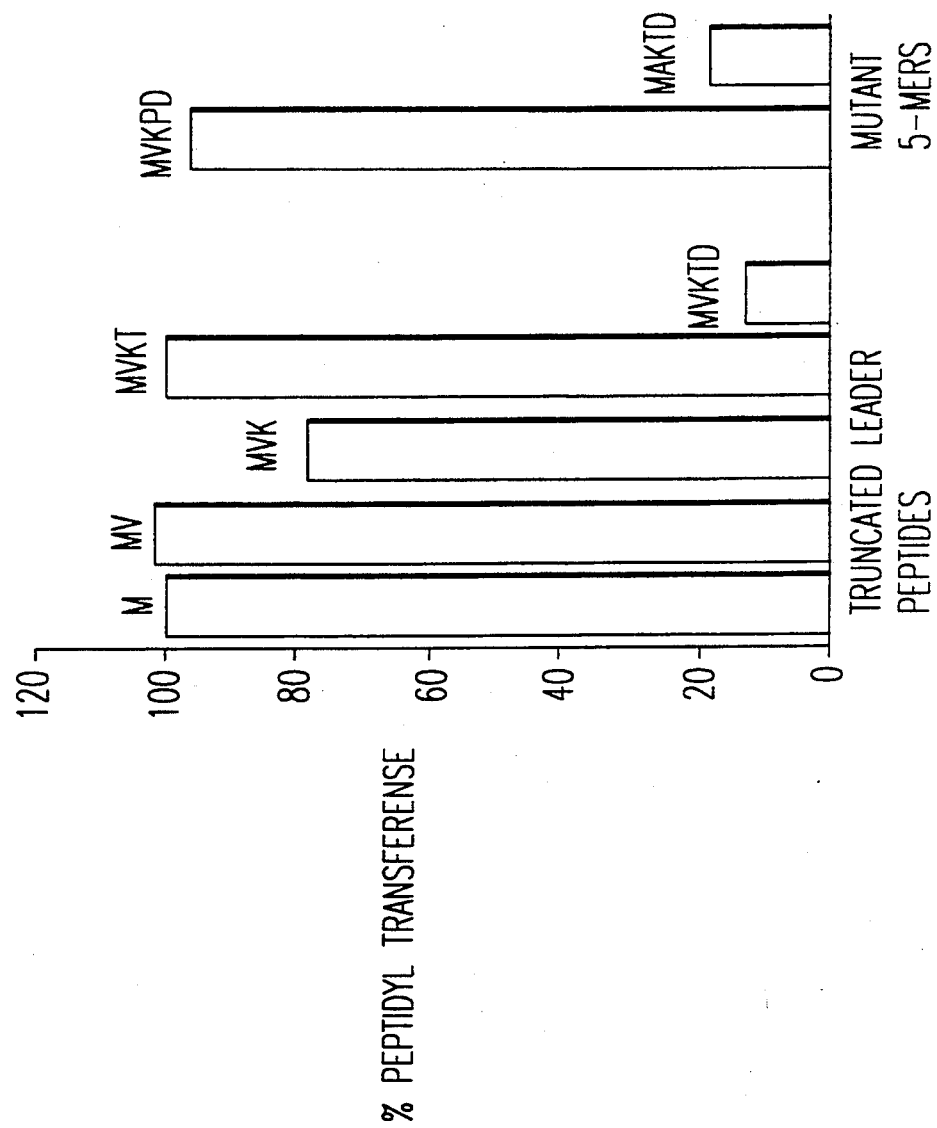
FIG. 6 graphically illustrates the degree of peptidyl transferase inhibition activity illustrated by the 5-mer peptide of the claimed invention as well as related peptides and mutants.

Peptide inhibitors were typically preincubated with the ribosomes prior to addition to the other reactants. Antibiotic inhibitors such as chloramphenicol were added to reaction mixes with the ribosomes but without the preincubation step. Preincubation of ribosomes with chloramphenicol failed to increase its inhibitory effect on peptidyl transferase, whereas peptide inhibition was greatly enhanced by the preincubation step. Peptidyl transferase reaction mixes were incubated on ice for 1 h, and were terminated by addition of 50 μl of 0.3M sodium acetate saturated with magnesium sulfate followed by 1 ml of ethyl acetate. The ethyl acetate phase was counted for radioactivity. All peptidyl transferase assays were performed in duplicate or triplicate, and the replicates varied by less than 5%. In separate experiments, the inhibitory activity of a single peptide preparation on a single ribosome preparation varied by as much as 10%. The peptides with amino acid substitutions showed different activities toward peptidyl transferase (FIG. 6). An Ala substitution at position 4 had no significant effect on 5-mer inhibition, while a Pro substitution at position 2 relieved essentially all inhibition.

The 50S subunit contains the target for the 5-mer peptide. Peptidyl transferase activity resides in the 50S subunit of bacterial ribosomes. To determine whether 5-mer inhibition was due to direct interaction with the catalytic (50S) subunit or required the 30S portion, ribosomes were dissociated and the 30S and 50S subunits were individually tested for peptidyl transferase and its response to the 5-mer (SEQ ID NO: 1) (Table 1). All peptidyl transferase activity of the dissociated ribosomes was due to the 50S subunits, and incubation of the 50S subunits with the 5-mer peptide resulted in inhibition that was approximately twice that observed with the 70S ribosomes. However, the 4-mer (SEQ ID NO: 5) and the reverse 5-mer had little effect on the peptidyl transferase activity of the 50S subunits.

The 5-mer (SEQ ID NO: 6) and 8-mer polypeptides of the claimed invention, the antibiotics and use thereof have been described, both generically and with respect to specific example. As noted, gross modification of the polypeptide may not be permissible, as peptidyl transferase inhibitory activity is lost. Modifications as described above, including the point variation of amino acids, the attachment of additional amino acids, the selective use of times and conditions, remain the scope of the invention, save as limited by the claims appended below.

---

What is claimed is:

1. A purified preparation of an amino acid sequence selected from the group consisting of
   Met-Val-Lys-Thr-Asp, (SEQ ID NO: 1)
   Met-Lys-Lys-Ala-Asp, (SEQ ID NO: 2)
   Met-Lys-Lys-Ser-Glu (SEQ ID NO: 3) and
   Met-Ser-Thr-Ser-Lys-Asn-Ala-Asp (SEQ ID NO: 4).

2. The preparation of claim 1, wherein said polypeptide inhibits at least 80 percent of the activity of peptidyl transferase.

3. An antibiotic composition comprising the purified preparation of claim 1 in a carrier, said preparation being present in antibiotic effective amounts.

4. A method of inhibiting peptidyl transferase in a microorganism, comprising contacting said microorganism in vitro with the antibiotic composition of claim 3.

5. A 5-mer polypeptide having the sequence
   Met-Val-Lys-Thr-Asp (SEQ ID NO: 1),
   Met-Lys-Lys-Ala-Asp (SEQ ID NO: 2) or
   Met-Lys-Lys-Ser-Glu (SEQ ID NO: 3).

6. An 8-mer polypeptide having the sequence
   Met-Ser-Thr-Ser-Lys-Asn-Ala-Asp (SEQ ID NO: 4).

* * * * *